United States Patent
Kimoto

(10) Patent No.: US 8,419,632 B2
(45) Date of Patent: Apr. 16, 2013

(54) BODY-INSERTABLE APPARATUS HAVING LIGHT ADJUSTMENT CONTROL UNIT AND IN-VIVO INFORMATION ACQUISITION SYSTEM

(75) Inventor: Seiichiro Kimoto, Akiruno (JP)

(73) Assignee: Olympus Medical Systems Corp., Tokyo (JP)

( * ) Notice: Subject to any disclaimer, the term of this patent is extended or adjusted under 35 U.S.C. 154(b) by 76 days.

(21) Appl. No.: 12/983,559

(22) Filed: Jan. 3, 2011

(65) Prior Publication Data

US 2011/0218399 A1 Sep. 8, 2011

Related U.S. Application Data

(63) Continuation of application No. PCT/JP2010/059974, filed on Jun. 11, 2010.

(30) Foreign Application Priority Data

Jun. 15, 2009 (JP) ................................ 2009-142171

(51) Int. Cl.
 *A61B 1/06* (2006.01)
 *A61B 1/04* (2006.01)
(52) U.S. Cl.
 USPC ............................................ 600/180; 348/69
(58) Field of Classification Search .................. 600/180, 600/118, 109; 348/65–76, 243, 309
See application file for complete search history.

(56) References Cited

U.S. PATENT DOCUMENTS

| | | | | |
|---|---|---|---|---|
| 4,868,645 | A | * | 9/1989 | Kobayashi ...................... 348/69 |
| 4,959,710 | A | * | 9/1990 | Uehara et al. .................. 600/109 |
| 5,010,395 | A | * | 4/1991 | Tsuji et al. ...................... 348/71 |
| 5,929,900 | A | * | 7/1999 | Yamanaka et al. .............. 348/65 |
| 6,597,390 | B1 | * | 7/2003 | Higuchi ........................... 348/65 |
| 6,607,301 | B1 | * | 8/2003 | Glukhovsky et al. ......... 374/175 |
| 6,612,981 | B2 | * | 9/2003 | Onishi et al. .................. 600/118 |
| 6,641,529 | B2 | * | 11/2003 | Kuranishi ..................... 600/160 |

(Continued)

FOREIGN PATENT DOCUMENTS

| EP | 1 852 051 A1 | 11/2007 |
|---|---|---|
| EP | 2 072 003 A2 | 6/2009 |

(Continued)

OTHER PUBLICATIONS

European Supplementary Search Report dated Apr. 12, 2012 from corresponding European Patent Application No. EP 10 78 9441.2.

(Continued)

*Primary Examiner* — John P Leubecker
(74) *Attorney, Agent, or Firm* — Scully Scott Murphy & Presser, PC

(57) ABSTRACT

A body-insertable apparatus to be inserted into a subject includes an illumination unit that illuminates an inside of the subject; an imaging device having an effective pixel region that has a predetermined size and on which an optical image of the inside of the subject illuminated by the illumination unit is formed, and having an optical black region at which the optical image is shielded; and a light adjustment control unit that adjusts an amount of light from the illumination unit to the effective pixel region based on pixel values of the effective pixel region of an image signal and pixel values of the optical black region of the image signal.

6 Claims, 14 Drawing Sheets

U.S. PATENT DOCUMENTS

| | | |
|---|---|---|
| 6,940,548 B2 | 9/2005 | Ying et al. |
| 7,042,487 B2 * | 5/2006 | Nakashima ............... 348/65 |
| 8,164,659 B2 * | 4/2012 | Mori et al. ............... 348/245 |
| 2006/0287580 A1 * | 12/2006 | Jo et al. ............... 600/160 |
| 2007/0195164 A1 * | 8/2007 | Fukuyama ............... 348/65 |
| 2009/0303319 A1 | 12/2009 | Sato et al. |

FOREIGN PATENT DOCUMENTS

| | | |
|---|---|---|
| JP | 63-294826 | 12/1988 |
| JP | 07-194528 | 8/1995 |
| JP | 10-1899312 | 7/1998 |
| JP | 2001-061823 | 3/2001 |
| JP | 2001-218728 A | 8/2001 |
| JP | 2002-219099 | 8/2002 |
| JP | 2002-263064 | 9/2002 |
| JP | 2002-345743 | 12/2002 |
| JP | 2004-321610 | 11/2004 |
| JP | 2006-140642 | 6/2006 |
| KR | 10-2006-0132445 | 12/2006 |
| WO | WO 2008/102803 A1 | 8/2008 |

OTHER PUBLICATIONS

Partial English Translation of JP 2002-345743.
Decision of a Patent Grant dated Feb. 15, 2011 together with English translation.
International Search Report dated Aug. 10, 2010.

* cited by examiner

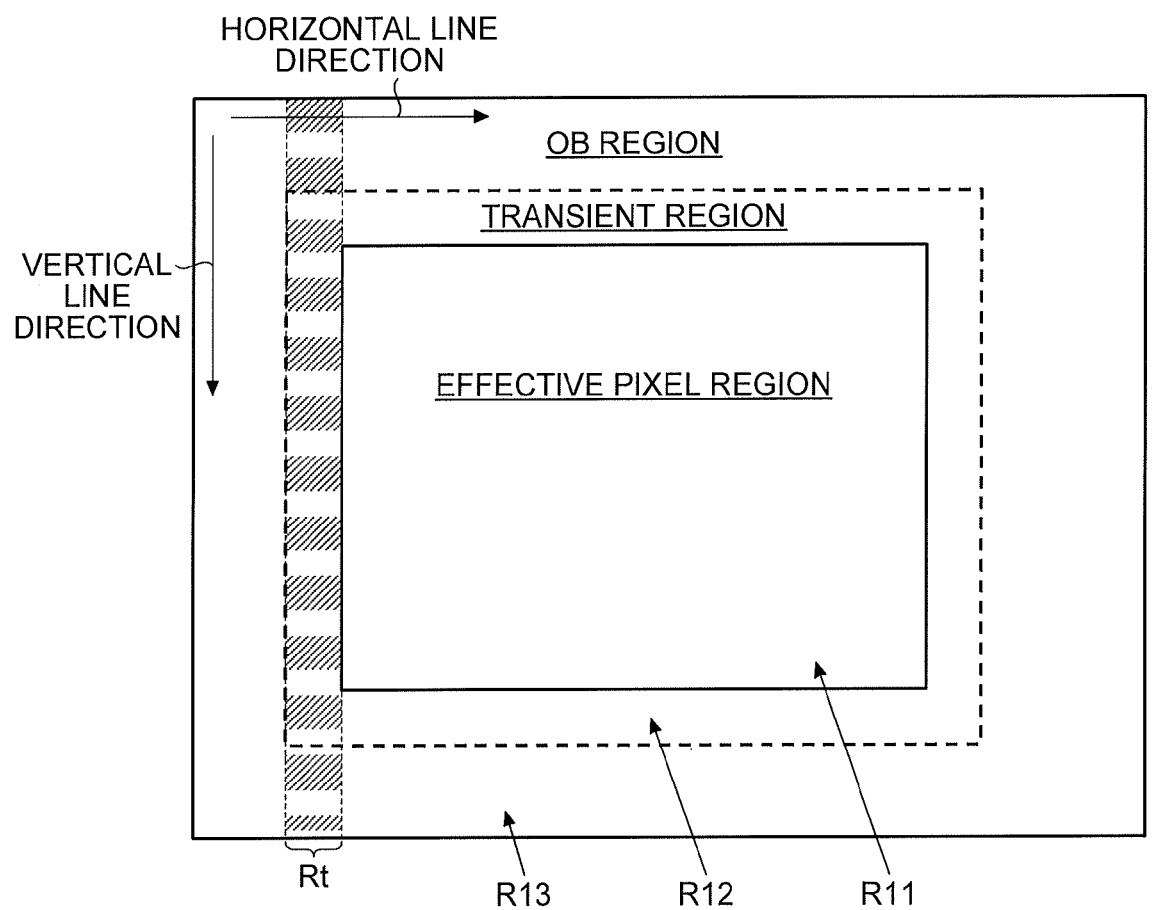

BODY-INSERTABLE APPARATUS HAVING LIGHT ADJUSTMENT CONTROL UNIT AND IN-VIVO INFORMATION ACQUISITION SYSTEM

CROSS-REFERENCE TO RELATED APPLICATIONS

This application is a continuation of PCT international application Ser. No. PCT/JP2010/059974 filed on Jun. 11, 2010 which designates the United States, incorporated herein by reference.

BACKGROUND OF THE INVENTION

1. Field of the Invention

The present invention relates to a body-insertable apparatus and an in-vivo acquisition system.

2. Description of the Related Art

Conventionally, there are body-insertable apparatuses that are perorally inserted into a subject, such as a living body, and acquire in-vivo images of the subject. In such a body-insertable apparatus, for example, an illumination unit, an image sensor, and a transmission circuit that transmits acquired images by radio to a receiving device, which is arranged outside the subject, are housed in a capsule-shaped casing. A body-insertable apparatus including such an imaging means is conventionally configured to correct the value of optical black (OB) in an acquired image, i.e., to perform a black level correction (hereinafter, "OB correction") in the apparatus (see Japanese Laid-open Patent publication No. 2006-140642).

For example, an image sensor with which a body-insertable apparatus is equipped with acquires an image of an object that is illuminated with illumination light from an illumination unit. After signal processing, such as correlated double sampling, is performed on an analog image signal that is output from the image sensor, the analog image signal is converted by an A/D converter to a digital signal. After digital signal processing, such as OB correction and offset adjustment, are performed on the digitized image signal, the image signal is sent to a transmission circuit and then transmitted from the transmission circuit to the outside of the subject via an antenna. The OB correction can be performed by simply dividing a digital signal by an offset or by performing a feedback process on the analog signal.

The body-insertable apparatus is also equipped with a light adjustment circuit that adjusts the amount of light of the illumination unit. The light adjustment circuit performs a light measurement process on an image signal obtained by an image sensor. In the light measurement process, the brightness of a target image is obtained using a simple average, weighting average, and peak value of luminance of a predetermined region, or using a value calculated from combinations thereof. In addition, the brightness of a target image can be obtained using the signal level of each pixel. The image signal to be processed may be an analog signal or a digital signal.

The light adjustment circuit adjusts the amount of light (the amount of light emission or light emission time) of the illumination unit for capturing of an image of the next frame according to the result obtained by the light measurement process. For example, when the result obtained by the light measurement process does not reach a pre-set target value, the light adjustment circuit increases the amount of light of the illumination unit for capturing of an image of the next frame. In contrast, when the result obtained by the light measurement process exceeds the pre-set target value, the light adjustment circuit reduces the amount of light of the illumination unit for capturing of an image of the next frame. By adjusting the amount of light of the illumination unit for capturing of an image of the next frame according to the brightness of the image of the next frame as described above, an image in which approximately equal brightness is maintained can be acquired even if, for example, the distance between the body-insertable apparatus and the object varies.

SUMMARY OF THE INVENTION

A body-insertable apparatus according to an aspect of the present invention is to be inserted into a subject, and includes an illumination unit that illuminates an inside of the subject; an imaging device having an effective pixel region on which an optical image of the inside of the subject illuminated by the illumination unit is formed and an optical black region at which the optical image is shielded, the effective pixel region having a predetermined size; and a light adjustment control unit that adjusts an amount of light from the illumination unit to the effective pixel region based on pixel values of the effective pixel region of an image signal and pixel values of the optical black region of the image signal.

An in-vivo information acquisition system according to another aspect of the present invention includes a body-insertable apparatus and an external device. The body-insertable apparatus includes an illumination unit that illuminates an inside of a subject; an imaging device having an effective pixel region on which an optical image of the inside of the subject illuminated by the illumination unit and an optical black region at which the optical image is shielded, the effective pixel region having a predetermined size; and a light adjustment control unit that adjusts an amount of light from the illumination unit to the effective pixel region based on pixel values of the effective pixel region of an image signal and pixel values of the optical black region of the image signal. The external device receives the image signal transmitted from the body insertable apparatus and displays the image signal.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 14 is a diagram illustrating a conception of an image signal of one frame that is transmitted by a capsule medical apparatus in a fourth embodiment of the present invention.

DETAILED DESCRIPTION OF THE PREFERRED EMBODIMENTS

Figure 1:
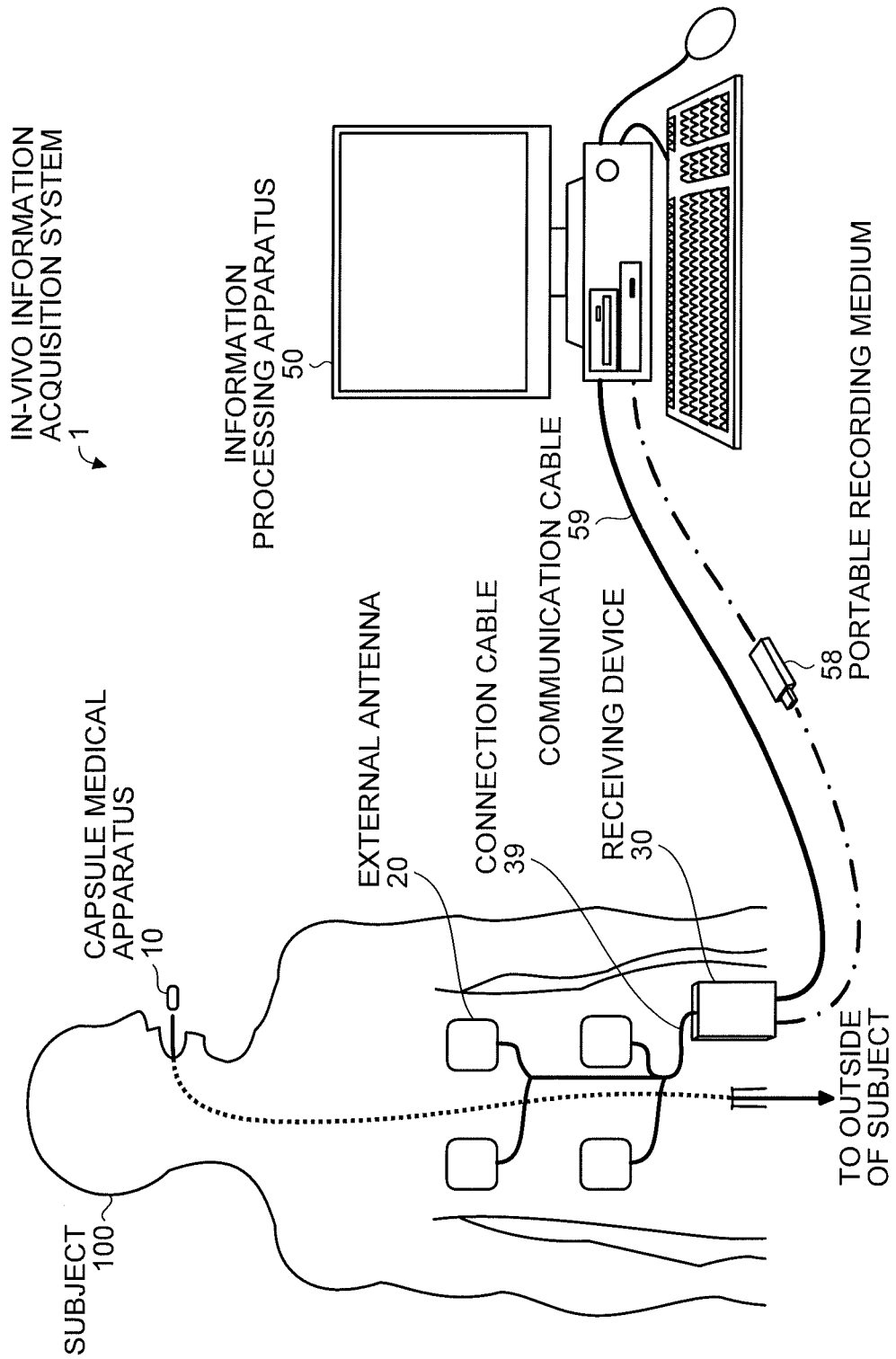
FIG. 1 is a schematic diagram of a general configuration of an in-vivo information acquisition system according to a first embodiment of the present invention.

Exemplary embodiments of the present invention will be described in detail below with reference to the drawings. In the following description, each drawing only schematically represents shapes, sizes, and positional relationships such that the contents of the present invention can be understood; therefore, the present invention is not limited to the shapes, sizes and positional relationships that are illustrated in the drawings.

First Embodiment

A configuration and operations of an in-vivo information acquisition system according to a first embodiment of the present invention will be described in detail below using the drawings. In the first embodiment, a case is taken as an example in which a capsule medical apparatus 10, which is perorally inserted into a subject 100 and acquires in-vivo information of the subject 100 (subject in-vivo information) while moving from the esophagus to the anus of the subject 100, is used as a body-insurable apparatus. However, the present invention is not limited to this. Various body-insertable apparatuses, such as a capsule medical apparatus that captures some in-vivo information of the subject 100 while remaining in various internal organs including the stomach or intestine of the subject 100, can be used. In the first embodiment, images (subject in-vivo images) acquired by capturing images using an imaging unit 12, which will be described below, are taken as an example of the in-vivo information acquired by the capsule medical apparatus 10. However, the present invention is not limited to this. Various types of information, such as the internal temperature, pressure, and pH value of the subject may be used as in-vivo information.

Configuration

FIG. 1 is a schematic diagram of a general configuration of an in-vivo information acquisition system 1 according to the first embodiment. As depicted in FIG. 1, the in-vivo information acquisition system 1 includes the capsule medical apparatus 10, sized such that it can be swallowed by the subject 100; a receiving device 30 that can receive an image signal that is transmitted as a radio signal from the capsule medical apparatus 10; and an information processing apparatus 50 that can input or output data via a radio interface, such as a wired interface using the receiving device 30 and a communication cable 59, such as a USB (universal serial bus) cable, via a radio interface, such as Bluetooth (registered trademark), or via a portable recording medium 58, such as a flash memory (registered trademark).

An external antenna 20 is connected to the receiving device 30 via a connection cable 39 and a balun (not shown). The radio signal that is emitted from the capsule medical apparatus 10 is input to the receiving device 30 via the external antenna 20.

For example, the capsule medical apparatus 10 acquires subject in-vivo images regularly and transmits the acquired subject in-vivo images to the receiving device 30 each time in-vivo images are acquired. Thus, when a configuration is employed in which the receiving device 30 and the information processing apparatus 50 are connected to each other using a wired or wireless interface and subject in-vivo images received by the receiving device 30 are input to the information processing apparatus 50, subject in-vivo images that are acquired by the capsule medical apparatus 10 can be displayed by the information processing apparatus 50 to the user almost in real time. For example, when the cycle in which the capsule medical apparatus 10 acquires images is two frames per second, the information processing apparatus 50 acquires subject in-vivo images from the receiving device 30 in a cycle of at least twice per second and displays the subject in-vivo images. Accordingly, subject in-vivo images are displayed to the user almost in real time.

Figure 2:
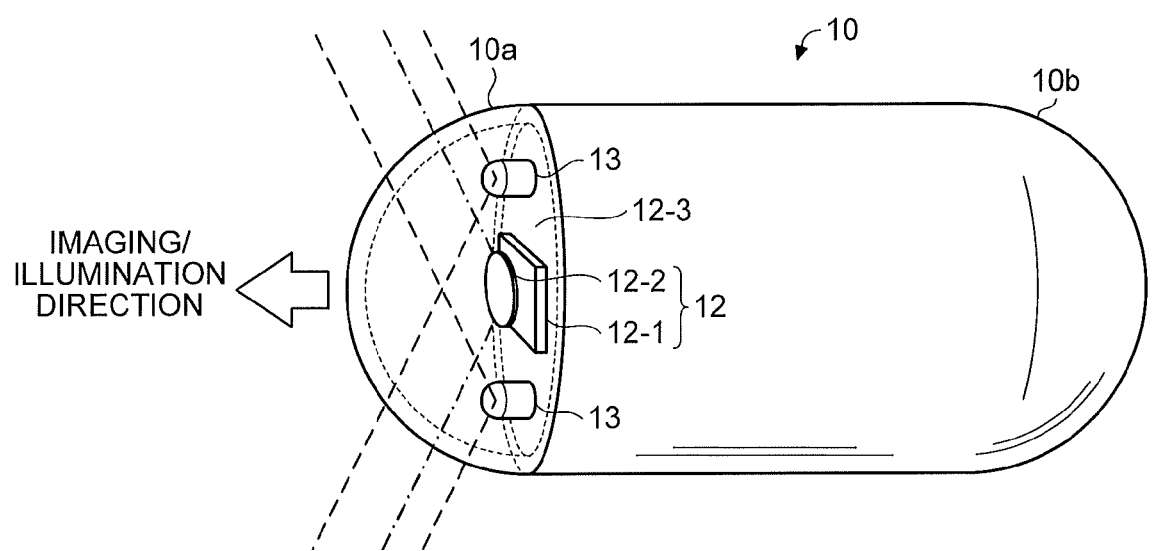
FIG. 2 is an outer view of a general configuration of a capsule medical apparatus according to the first embodiment of the present invention.

FIG. 2 is an outer view of a general configuration of the capsule medical apparatus 10 according to the first embodiment. As depicted in FIG. 2, the capsule medical apparatus 10 is housed in a capsule-shaped housing (casing) consisting of a roughly cylindrical or an ellipsoidal housing 10b with one dome-shaped hemisphere end and one open end; and a semi-sphere cap 10a that is fitted to the opening of the housing 10b, thereby sealing the housing 10b watertight. The capsule-shaped housing (10a and 10b) is sized such that, for example, it can be swallowed by the subject 100. In the first embodiment, at least the cap 10a is formed of a transparent material.

The capsule medical apparatus 10 includes the imaging unit 12 as a means for capturing in-vivo images of the subject 100 and an illumination unit 13 as a means for illuminating an inside of the subject 100 when capturing images. The imaging unit 12 includes an imaging device 12-1, such as a CCD camera or a CMOS camera, that captures in-vivo images of the subject 100 and generates image data of the in-vivo images; and an optical system 12-2 that includes an objective lens arranged on the light receiving side of the imaging device 12-1 and a light shielding board that defines an effective pixel region. As depicted in FIG. 2, the imaging device 12-1 and the optical system 12-2 are mounted on a circuit board 12-3 that includes drive circuits for driving the imaging device 12-1 and the optical system 12-2. The circuit board 12-3 is arranged on the side of the cap 10a in the capsule-shaped housing (10a and 10b). As depicted in FIG. 2, the imaging direction of the imaging unit 12 and the illumination direction of the illumination unit 13 extend to the outside of the capsule medical apparatus 10 via the cap 10a. Thus, while the illumination unit 13 is illuminating the insided of the subject 100, the imaging unit 12 can capture in-vivo images of the subject 100.

The illumination unit 13 for illuminating the inside of the subject 100 with light when capturing images and a drive circuit for the illumination unit 13 are also mounted on the circuit board 12-3. The drive circuits for the imaging device 12-1 and the illumination unit 13 operate under the control of a control circuit 11 and a light adjustment computing unit 16, which will be described below, and, for example, image signals of the subject in-vivo images are generated regularly (for example, two frames per second) and the image signals are input to an analog signal processing circuit 14, which will be described below. In the following descriptions, it is assumed that the imaging device 12-1 and the illumination unit 13, respectively, include their own drive circuits.

In the first embodiment, the capsule medical apparatus 10 including one pair of the imaging unit 12 and the illumination unit 13 is taken as an example. However, the present invention is not limited to this. For example, a capsule medical apparatus including multiple pairs of an imaging unit and an illumination unit, i.e., a pantoscopic capsule medical apparatus, may be employed. For example, a binocular capsule medical apparatus includes a housing that is hollow and cylindrical with both ends open to which transparent caps are fitted, respectively. An imaging unit and an illumination unit are provided at each of the open ends such that they face the outside of the capsule medical apparatus through their respective caps.

Figure 3:
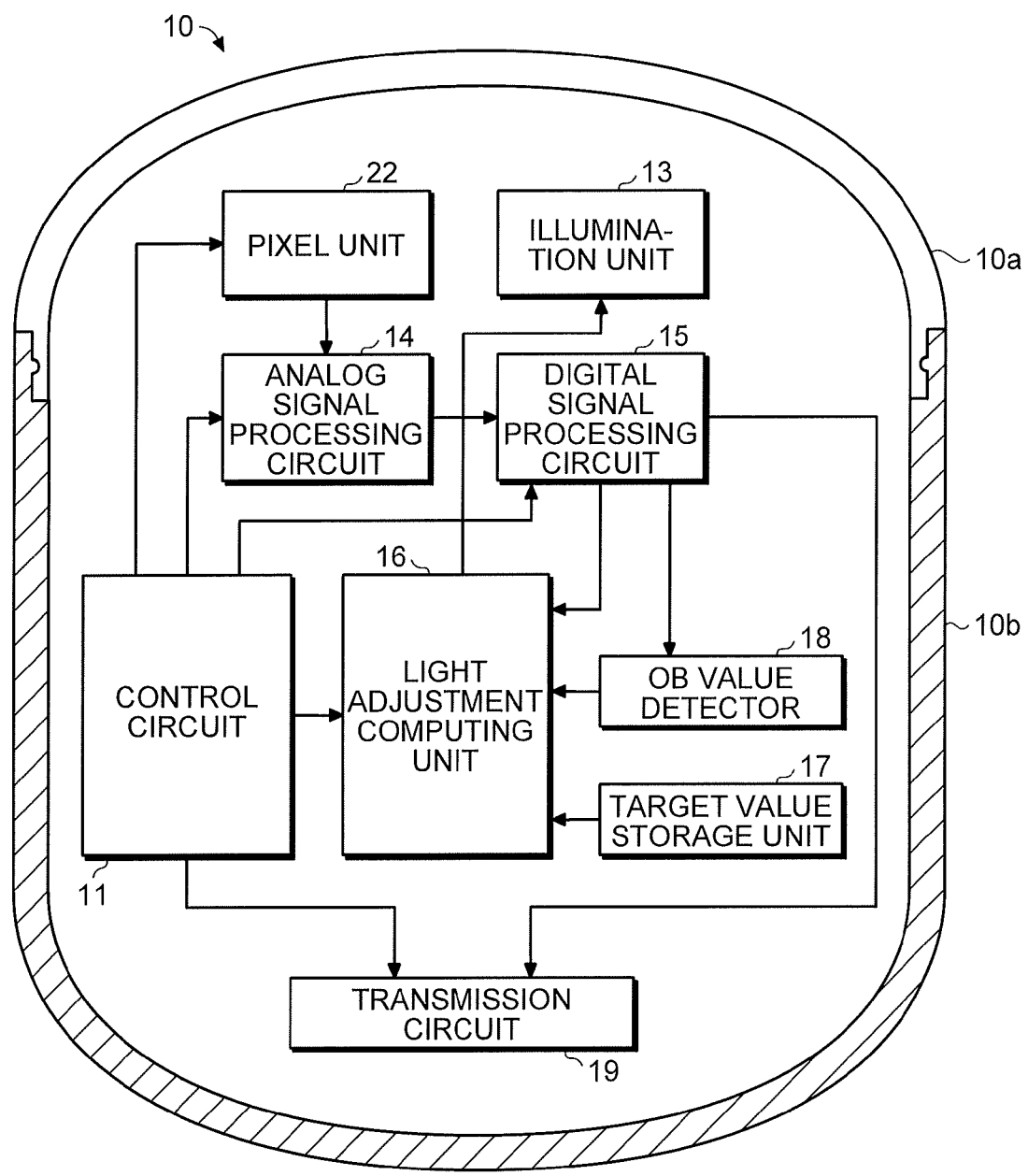
FIG. 3 is a block diagram of a schematic internal configuration of the capsule medical apparatus according to the first embodiment of the present invention.

A general internal configuration of the capsule medical apparatus 10 according to the first embodiment will be described using FIG. 3. FIG. 3 is a block diagram of the general internal configuration of the capsule medical apparatus 10 according to the first embodiment.

As depicted in FIG. 3, the capsule medical apparatus 10 includes the control circuit 11, a pixel unit 22, the illumination unit 13, the analog signal processing circuit 14, a digital signal processing circuit 15, the light adjustment computing unit 16, a target value storage unit 17, an OB value detector (black level index detector) 18, and a transmission circuit 19. A battery (not shown) and a power supply circuit are installed in the capsule medical apparatus 10 and power is supplied to each unit in the capsule medical apparatus 10.

The control circuit 11 controls each unit in the capsule medical apparatus 10. The pixel unit 22 generates an image signal of a subject in-vivo image under the control of the control circuit 11 and then inputs the image signal to the analog signal processing circuit 14. The illumination unit 13 illuminates an object by emitting illumination light according to the imaging timing of the imaging unit 12 under the control of the light adjustment computing unit 16, which will be described below.

After performing analog signal processing, such as correlated double sampling, on an input analog signal under the control of the control circuit 11, the analog signal processing circuit 14 inputs the image signal after the processing to the digital signal processing circuit 15. The digital signal processing circuit 15 converts the input analog image signal to a digital signal under the control of the control circuit 11 and performs digital signal processing, such as OB correction and offset adjustment, on the digital image signal after the conversion. The digital signal processing circuit 15 inputs the image signal after the processing to each of the light adjustment computing unit 16, the OB value detector 18, and the transmission circuit 19. The transmission circuit 19 transmits the input image signal as a radio signal to the outside of the capsule medical apparatus 10 under the control of the control circuit 11 each time an image signal is input.

The OB value detector 18 calculates a value serving as an index of the black level of an image signal generated by the corresponding imaging unit 12 (hereinafter, "OB value") from pixel values of a part of or pixel values of the whole of a non-exposed region (hereinafter, "OB region") in the image signal after the digital signal processing, which is input from the digital signal processing circuit 15. The OB region will be described in detail below using FIG. 4.

The light adjustment computing unit 16 performs a light measurement process on the pixel values of an effective pixel region $R_{eff}$ (or a part of the effective pixel region $R_{eff}$) of an image signal after the digital signal processing, which is input from the digital signal processing circuit 15, and acquires a measured light value representing how much luminance or lightness a target frame has. In other words, the light adjustment computing unit 16 also functions as a measured light value calculator that calculates a measured light value from an image signal generated by the imaging unit 12.

The target value storage unit 17 stores a target value for driving the illumination unit 13, i.e., a target value of a drive amount for driving the illumination unit 13. The light adjustment computing unit 16 adjusts the amount of illumination light, which is emitted from the illumination unit 13 when capturing of an image of the next frame, by performing a light adjustment arithmetic operation according to the OB value obtained from the image signal of the preceding frame, the measured light value obtained by the light measurement process, and the target value stored in the target value storage unit 17, such that the black level of the image signal obtained as the next frame becomes the target black level.

For example, in the light adjustment arithmetic operation, the target value in the light adjustment control on the illumination unit 13 can be corrected by adding the OB value to the target value, which is read from the target value storage unit 17. The light adjustment computing unit 16 compares the target value after correction, which is obtained by this addition (hereinafter "corrected target value"), with the measured light value of the effective pixel region $R_{eff}$ (or a part of the effective pixel region $R_{eff}$) and, according to the result of the comparison, drives the illumination unit 13 and performs light adjustment control on the illumination unit 13, thereby adjusting the amount of illumination light emitted by the illumination unit 13 when capturing of an image of the next frame. In this manner, light adjustment control can be performed on the illumination unit 13 while excluding variations of the OB value of the preceding frame.

In another light adjustment arithmetic operation method, for example, the measured light value is corrected by subtracting the OB value from the measured light value of the targeted effective pixel region $R_{eff}$ (or a part the effective pixel region $R_{eff}$). The light adjustment computing unit 16 compares the measured light value after the correction obtained by the subtraction (hereinafter, "corrected measured light value") with the target value read from the target value storage unit 17 and, according to the result of the comparison, performs light adjustment control on the illumination unit 13 and drives the illumination unit 13, thereby adjusting the amount of illumination light emitted by the illumination unit 13 upon capturing an image of the next frame. In this manner, as described above, light adjustment control can be performed on the illumination unit 13 while excluding variation of the OB value of the preceding frame.

Accordingly, the light adjustment computing unit 16, the target value storage unit 17, and the OB value detector 18 function as a light adjustment controller that adjusts the amount of light from the illumination unit 13 according to the pixel values of the effective pixel region $R_{eff}$ of the image signal and the pixel values of the OB region $R_{OB}$ of the image signal. By correcting the difference between the measured light value and the target value of the effective pixels according to the OB value acquired from the preceding frame as described above, a stable light adjustment process can be performed that does not depend on the distance between the object and the capsule medical apparatus 10, on the characteristics of the imaging unit 12, nor on the characteristics of the illumination unit 13. Accordingly, image signals having a stable black level can be generated. In addition, because it is not necessary to perform OB correction on image signals in the capsule medical apparatus 10, the number of arithmetic operations performed in the capsule medical apparatus 10 can be reduced, which reduces the power consumption of the capsule medical apparatus 10. Making the OB value close to the target value means making the black level of an image signal a given level (the target level).

Figure 4:
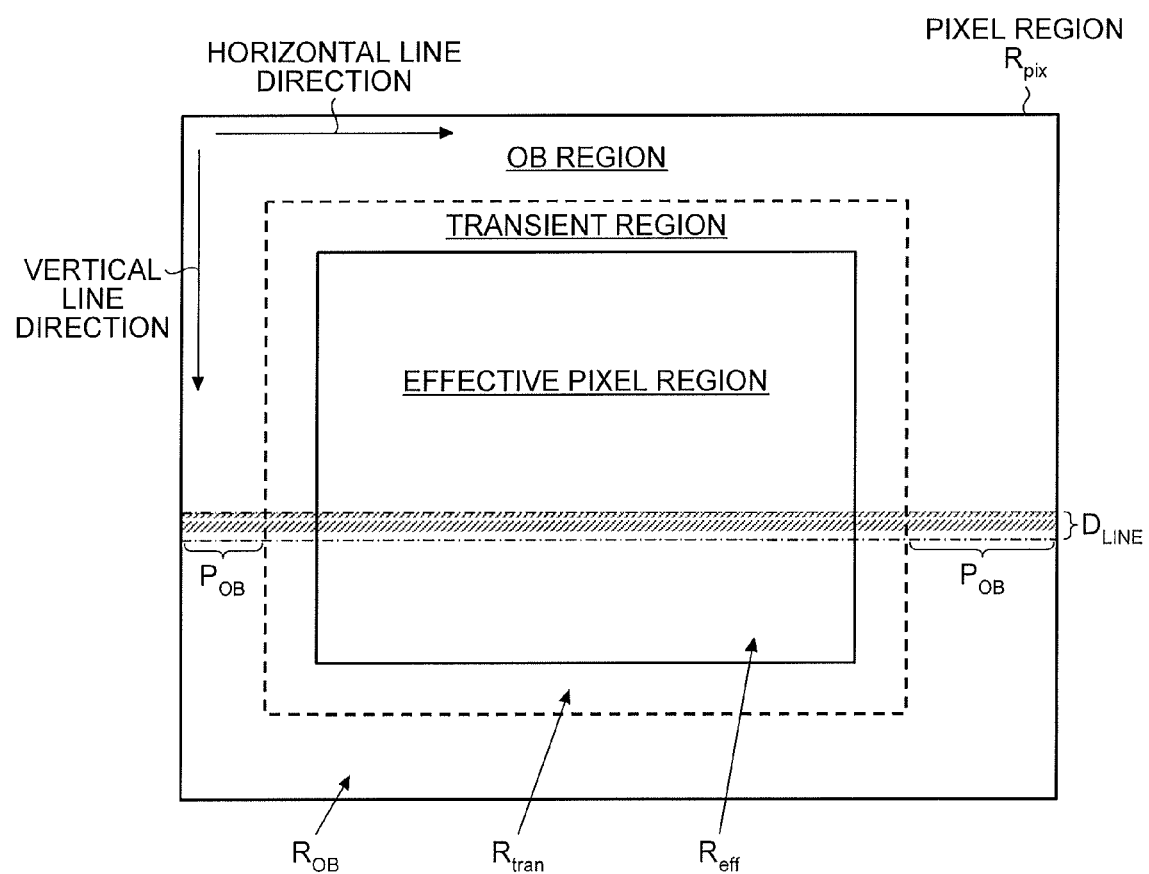
FIG. 4 is a diagram of an example of a pixel region of an imaging unit in the first embodiment of the present invention.

The OB region in the image signal in the first embodiment will be described in detail below using FIG. 4. FIG. 4 is a diagram of an example of a pixel region of the imaging unit 12 in the first embodiment.

As depicted in FIG. 4, a pixel region $R_{pix}$ includes an effective pixel region $R_{eff}$ that is not shielded from light, an OB region $R_{OB}$ that is sufficiently shielded from light, and a transient region $R_{tran}$ that is on the border between the effective pixel region $R_{eff}$ and the OB region $R_{OB}$ and is not sufficiently shielded. The OB region $R_{OB}$ is arranged to surround the effective pixel region $R_{eff}$. Thus, for example, the n line of an image signal Dn containing the effective pixel region $R_{eff}$ contains multiple pixels that belong to the OB region $R_{OB}$ (hereinafter, a pixel in the OB region $R_{OB}$ is referred to as an "OB pixel") at the head and end of the line.

An image signal obtained by reading one frame by each line sequentially is input from the pixel unit 22 to the digital signal processing circuit 15 via the analog signal processing circuit 14. Thereafter, the predetermined digital signal processing are performed on the image signal and the image signal is then output to the transmission circuit 19 and the OB value detector 18.

The OB value detector 18 acquires the values of the OB region $R_{OB}$ of each line in the image signal output from the digital signal processing circuit 15. The OB value detector 18 calculates an OB value used for OB correction on a target line by using one or more values out of the acquired values of the OB region $R_{OB}$ in each respective line of the image signal. In other words, the OB value detector 18 calculates an OB value of each line from one or more pixel values of the OB pixels $P_{OB}$ of each respective line. As an OB value, for example, the pixel value of a specific OB pixel $P_{OB}$ in the horizontal direction of each line may be used or a simple average, weighted average, or the median of the pixel values of a specific OB region $R_{OB}$ of each line may be used. The OB value detector 18 inputs the acquired OB value to the light adjustment computing unit 16.

In the above description, an OB value to be used is obtained per line, but the present invention is not limited to this. Various modifications may be employed. For example, an OB value to be used may be obtained per some pixels in one line, an obtained OB value may be shared by some lines, or an OB value to be used may be obtained per specific two-dimensional region.

Figure 5:
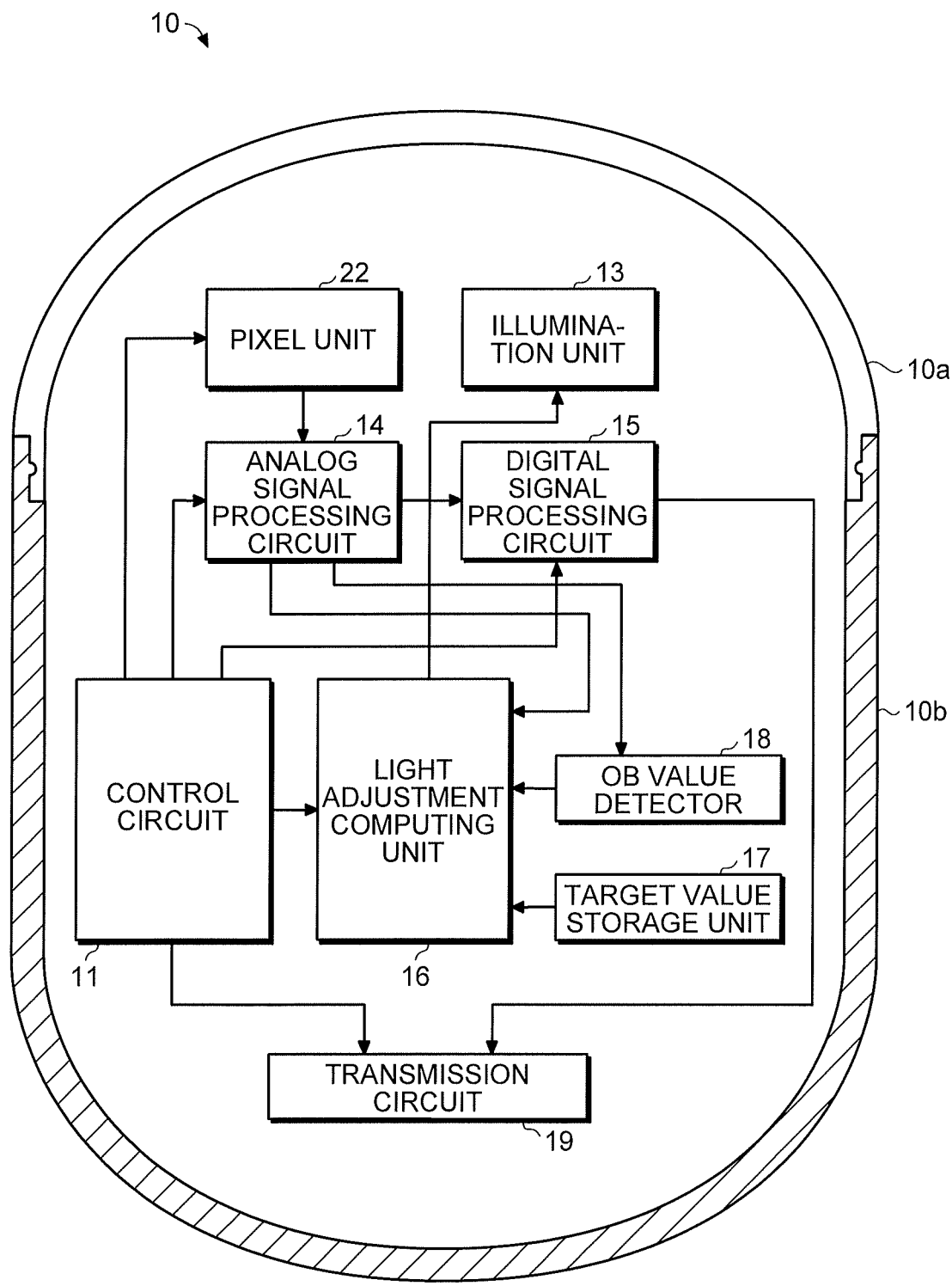
FIG. 5 is a schematic block diagram of another mode of the capsule medical apparatus according to the first embodiment of the present invention.

In the above description, the OB value is calculated from the digital image signal, but the present invention is not limited to this. An OB value may be calculated from an analog signal output from the analog signal processing circuit 14. In this case, as depicted in FIG. 5, an image signal output from the analog signal processing circuit 14 is input to the light adjustment computing unit 16 and the OB value detector 18. The light adjustment computing unit 16 performs a light measurement process on the input analog signal and acquires a measured light value of an effective pixel. The OB value detector 18 acquires an OB value from the input analog image signal and inputs the OB value to the light adjustment computing unit 16. The light adjustment computing unit 16 drives the illumination unit 13 while performing light adjustment control according to the input OB value, the acquired measured light value, and the read target value when capturing of an image of the next frame. FIG. 5 is a schematic block diagram of another mode of the capsule medical apparatus 10 according to the first embodiment. Because the OB value can be acquired using the same method as the above-described method for an analog signal In FIG. 5, detailed descriptions thereof are omitted here.

Operation

Figure 6:
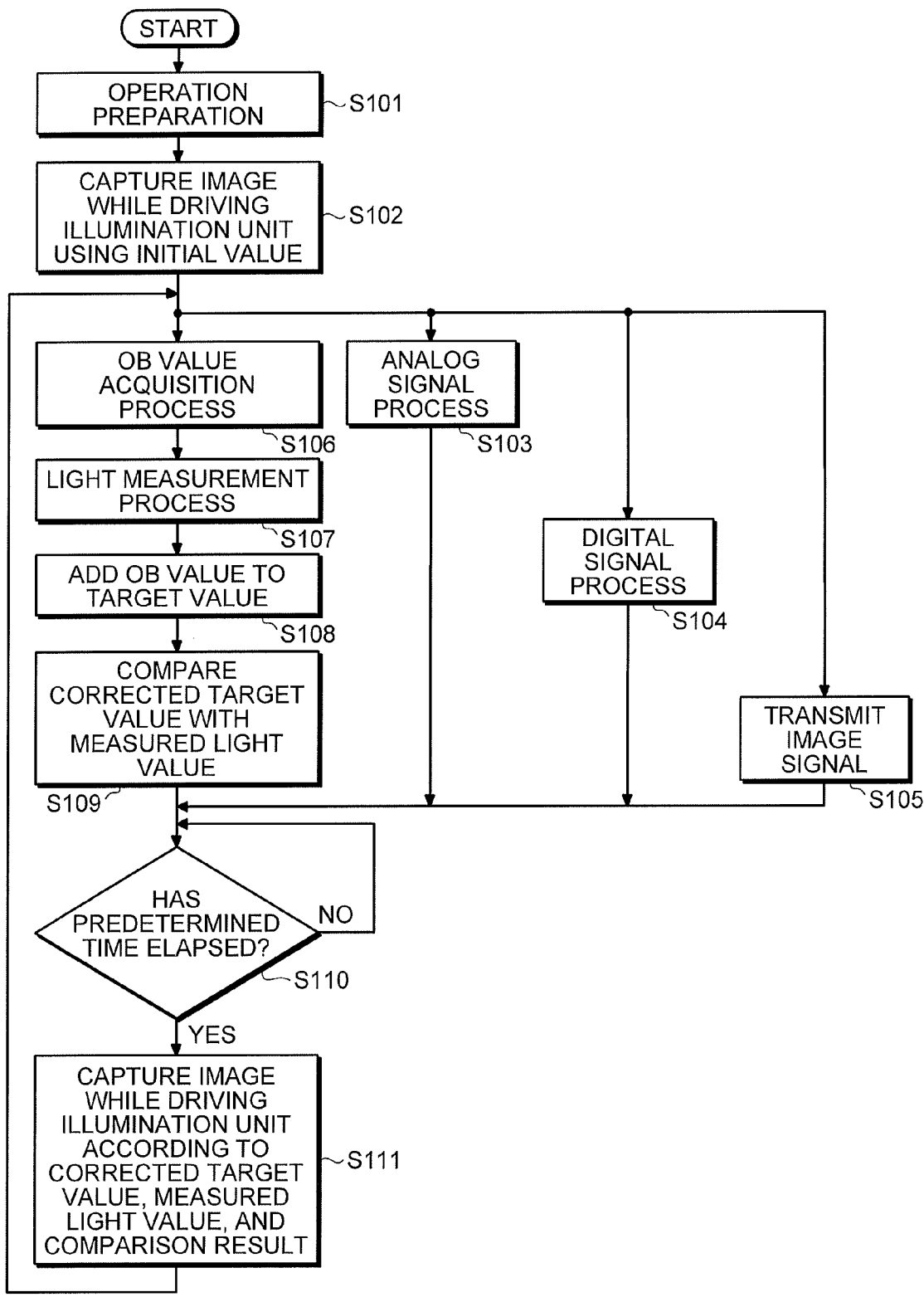
FIG. 6 is a flowchart illustrating general operations of the capsule medical apparatus according to the first embodiment of the present invention.

The operations of the capsule medical apparatus 10 according to the first embodiment will be described in detail below using the drawings. FIG. 6 is a flowchart illustrating general operations of the capsule medical apparatus 10 according to the first embodiment.

As illustrated in FIG. 6, after the capsule medical apparatus 10 is started, it performs an operation preparation (step S101). Once the operation preparation is completed, the capsule medical apparatus 10 drives the illumination unit 13 using an initial value stored in, for example, a memory (not shown) and drives the imaging unit 12 to capture an in-vivo image of the subject 100 (step S102). Subsequently, the capsule medical apparatus 10 inputs an analog image signal generated by the imaging unit 12 and performs the predetermined analog signal processing (step S103), and the capsule medical apparatus 10 inputs the image signal on which the analog signal processing is performed to the digital signal processing circuit 15 and performs the predetermined digital signal processing (step S104). The image signal on which the digital signal processing is performed is input to the transmission circuit 19 and then transmitted by radio (step S105) and input to the OB value detector 18.

In the capsule medical apparatus 10, the OB value detector 18 then performs an OB value acquisition process (step S106). In the OB value acquisition process, for example, as described above, the OB value detector 18 acquires, as an OB value, the pixel value of a specific OB pixel $P_{OB}$ of each line in the horizontal direction. However, the present invention is not limited to this. Various modifications may be employed. For example, OB values to be used are obtained each for multiple pixels in one line, an obtained OB value may be shared by some lines, or OB values to be used may be obtained each for a specific two-dimensional region.

In the capsule medical apparatus 10, the light adjustment computing unit 16 then performs a light measurement process on the pixels of the effective pixel region $R_{eff}$ (or a part of the effective pixel region $R_{eff}$) (step S107) and acquires a measured light value representing how much luminance or lightness a target frame has. The capsule medical apparatus 10 calculates a corrected target value by adding the OB value obtained at step S106 to the target value stored in the target value storage unit 17 (step S108). The capsule medical apparatus 10 then compares the corrected target value with the measured light value acquired by the light adjustment computing unit 16 (step S109). The processes at steps S103 to S109 may be performed simultaneously.

The capsule medical apparatus 10 then determines whether a predetermined time (for example, 0.5 seconds) has elapsed after the preceding image capturing time (step S110) and waits until the predetermined time has elapsed (NO at step S110). After the predetermined time has elapsed (YES at step S110), the capsule medical apparatus 10 drives the illumination unit 13 while performing light adjustment control on the illumination unit 13 according to the result of the comparison between the corrected target value and the measured light value at step S109 and drives the pixel unit 22 to capture in-vivo images of the subject 100 (step S111). Thereafter, the capsule medical apparatus 10 goes back to step S103 and then performs the same operations. The operations are continued until the battery installed in the capsule medical apparatus 10 runs out.

With the above-described configuration and operations, in the first embodiment, the amount of light from the illumination unit 13 can be adjusted according to a pixel value (measured light value) of an effective pixel region $R_{\mathit{eff}}$ in an image signal and a pixel value (OB value) of an OB region $R_{OB}$ in the image signal. Thus, even if the OB value varies depending on the pixel unit 22, variations in light adjustment control can be corrected automatically. As a result, the number of arithmetic operations in the capsule medical apparatus 10 can be reduced and a stable light adjustment process can be performed.

Multiple OB values used for correcting the target value or the measured light value may be used so as to correspond to multiple regions divided out of one frame. In addition, for example, OB-value variations between normal areas (i.e., between lines) are sufficiently small with respect to the light adjustment target value; therefore, one OB value may correspond to one frame. In other words, the OB value may be shared by lines in the same frame. In this case, an OB value to be shared may be an OB value obtained for any one line or area in one frame, or may be an average value of multiple OB values obtained for multiple lines or areas.

After the receiving device 30 or the information processing apparatus 50 arranged outside the subject 100 performs processes, such as OB correction, appropriately on the subject in-vivo image transmitted from the capsule medical apparatus 10, the subject in-vivo image is displayed to the user.

Modification 1-1

The above-described first embodiment can be applied to a capsule medical apparatus including multiple imaging systems each including an imaging device and an illumination unit, i.e., a pantoscopic capsule medical apparatus. Hereinafter, a case in which a binocular capsule medical apparatus is used will be described in detail below as Modification 1-1 of the first embodiment using the drawings.

Figure 7:
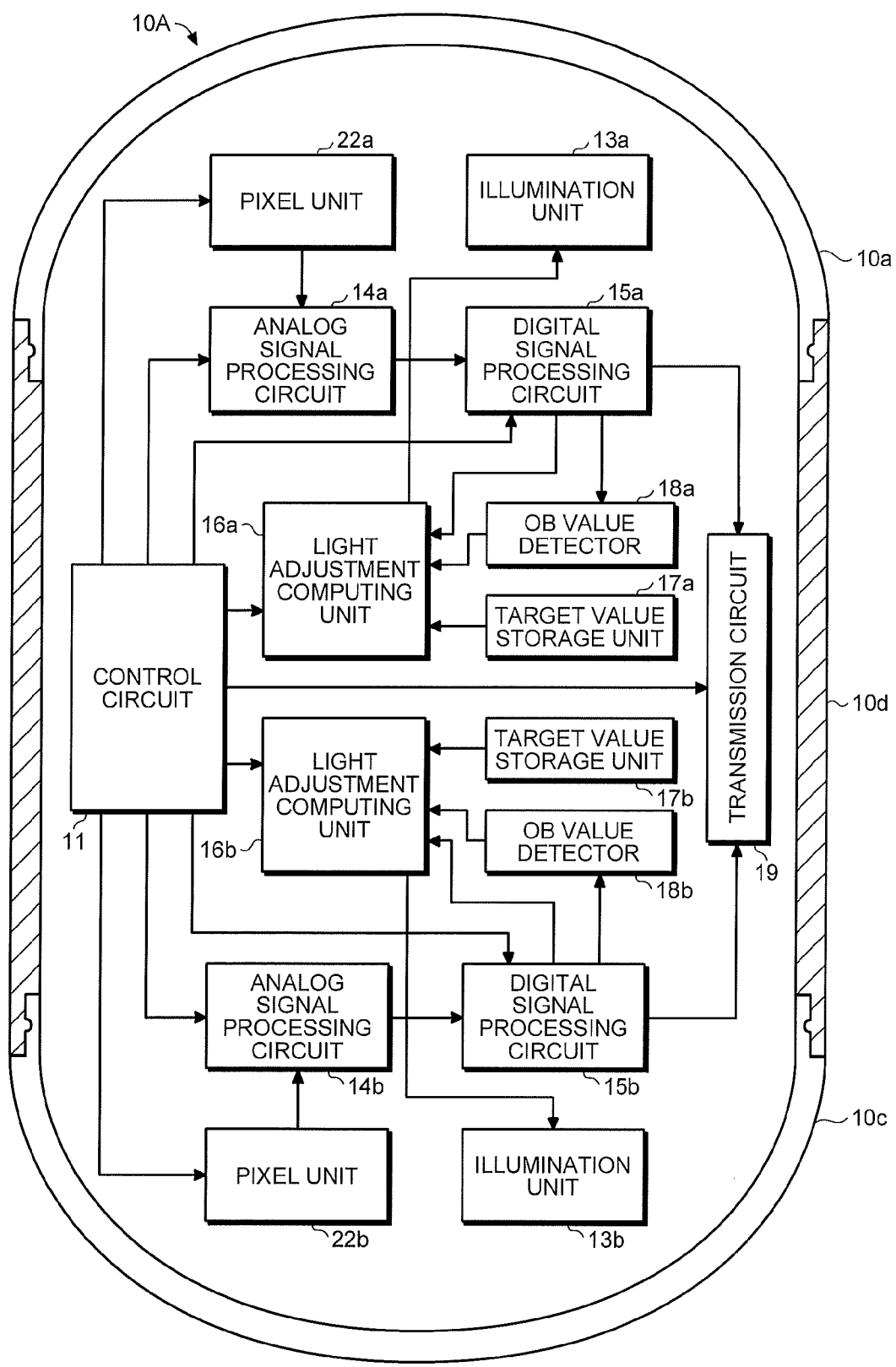
FIG. 7 is a block diagram of a general configuration of a capsule medical apparatus according to Modification 1-1 of the first embodiment of the present invention.

FIG. 7 is a block diagram of a general configuration of a capsule medical apparatus 10A of Modification 1-1. As depicted in FIG. 7, the capsule medical apparatus 10A includes a pixel unit 22a and an illumination unit 13a, which constitute one imaging system, and includes a pixel unit 22b and an illumination unit 13b, which constitutes another imaging system. The capsule medical apparatus 10A further includes an analog signal processing circuit 14a and a digital signal processing circuit 15a, which serve as a processing system that performs signal processing on an image signal generated by one imaging system, and further includes a light adjustment computing unit 16a, a target value storage unit 17a, and an OB value detector 18a which serve as a light adjustment mechanism that drives the illumination unit 13a of the imaging system while performing light adjustment control on the illumination unit 13a. In addition, the capsule medical apparatus 10A further includes an analog signal processing circuit 14b and a digital signal processing circuit 15b, which serve as a processing system that performs signal processing on an image signal generated by the other imaging system, and further includes a light adjustment computing unit 16b, a target value storage unit 17b, and an OB value detector 18b, which serve as a light adjustment mechanism that drives the illumination unit 13b of the imaging system while performing light adjustment control on the illumination unit 13b. The capsule medical apparatus 10A includes the control circuit 11 for controlling each unit and the transmission circuit 19 that transmits, by radio, image signals generated by each imaging system after the signal processing.

The above-described units are housed in a capsule-shaped casing consisting of a cylindrical housing 10d with both ends open, the cap 10a that is fitted to one of the openings of the housing 10d, and a cap 10c that is fitted to the other opening of the housing 10d and is equivalent to the cap 10a.

Imaging units 12a/12b, the illumination units 13a/13b, the analog signal processing circuits 14a/14b, the digital signal processing circuits 15a/15b, the light adjustment computing units 16a/16b, the target value storage units 17a/17b, and the OB value detectors 18a/18b are the same as the imaging unit 12, the illumination unit 13, the analog signal processing circuit 14, the digital signal processing circuit 15, the light adjustment computing unit 16, the target value storage unit 17, and the OB value detector 18, respectively, of the first embodiment. However, the pixel unit 22a and the illumination unit 13a illuminate/capturing an image of the side of the cap 10a, which is one of the caps, in the capsule medical apparatus 10A. The analog signal processing circuit 14a and the digital signal processing circuit 15a perform the predetermined signal processing on an image signal generated by the pixel unit 22a. The light adjustment computing unit 16a and the OB value detector 18a perform light adjustment control on the illumination unit 13a, and the target value storage unit 17a stores a target value for performing the light adjustment control on the illumination unit 13a. In contrast, the pixel unit 22b and the illumination unit 13b illuminate/capturing an image of the side of the cap 10a, which is the other cap, in the capsule medical apparatus 10A. The analog signal processing circuit 14b and the digital signal processing circuit 15b perform the predetermined signal processing on an image signal generated by the pixel unit 22b. The light adjustment computing unit 16b and the OB value detector 18b perform light adjustment control on the illumination unit 13b, and the target value storage unit 17b stores a target value for performing the light adjustment control on the illumination unit 13b.

As described above, the capsule medical apparatus 10A of Modification 1-1 includes light adjustment mechanisms (the light adjustment computing units 16a/16b and its neighboring units 17a/17b and 18a/18b) that respectively drive the illumination units 13a/13b of the multiple imaging systems while performing the light adjustment control on the illumination units 13a/13b. Accordingly, in Modification 1-1, light adjustment control can be performed on the illumination units 13a/13b in the respective imaging systems according to the corresponding pixel units 22a/22b; therefore, even if the OB value varies depending on each imaging device, variations in light adjustment control can be corrected automatically. As a result, in the capsule medical apparatus including multiple imaging devices, the number of internal arithmetic operations of each imaging device can be reduced and a stable light adjustment process can performed.

Other configurations, operations, and effects are the same as those of the above-described embodiment; therefore, detailed descriptions thereof are omitted here.

Modification 1-2

In the above-described Modification 1-1, mechanisms that drive the multiple illumination units 13a and 13b while performing light adjustment control on the illumination units 13a and 13b are provided individually, but the present invention is not limited to this. A configuration may be employed in which a part of or the entire light adjustment mechanism may be shared by multiple illumination units. This case will be described in detail below as Modification 1-2 of the first embodiment using the drawings.

Figure 8:
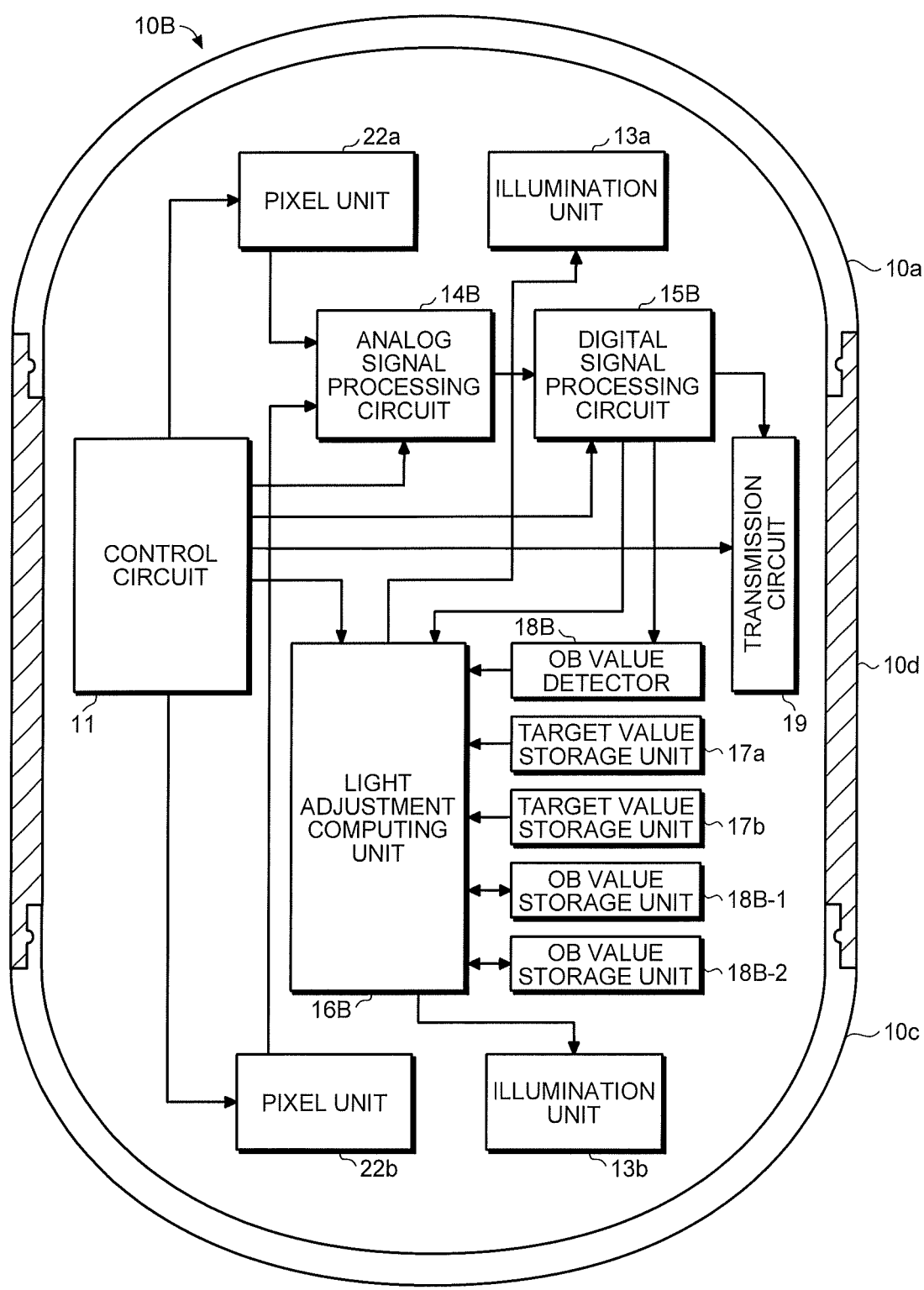
FIG. 8 is a block diagram of a general configuration of a capsule medical apparatus according to Modification 1-2 of the first embodiment of the present invention.

FIG. 8 is a block diagram of a general configuration of a capsule medical apparatus 10B according to Modification 1-2. As depicted in FIG. 8, the capsule medical apparatus 10B includes, in a capsule-shaped casing (10a, 10c, and 10d) the same as that of the above-described Modification 1-1, two imaging systems (the pixel units 22a/22b and the illumination units 13a/13b) and a processing system (an analog signal processing circuit 14B and a digital signal processing circuit 15B) and a light adjustment system (a light adjustment computing unit 16B and an OB value detector 18B) that are shared by the two imaging systems.

However, in Modification 1-2, unique values corresponding respectively to the pixel units 22a/22b are used for the target values for performing light adjustment control on the illumination units 13a/13b in the respective imaging systems. Thus, as depicted in FIG. 8, the capsule medical apparatus 10B includes the target value storage unit 17a that stores the target value for performing light adjustment on the illumination unit 13a and the target value storage unit 17b that stores the target value for performing light adjustment on the illumination unit 13b.

Modification 1-2 further includes an OB value storage unit 18B-1 for temporarily storing the OB value and the measured light value, which are used when performing light adjustment control on the illumination unit 13a, and an OB value storage unit 18B-2 for temporarily storing the OB value and the measured light value, which are used when performing light adjustment control on the illumination unit 13b.

The capsule medical apparatus 10B further includes the control circuit 11, the transmission circuit 19 for transmitting, by radio, image signals generated by the imaging systems after the image processing.

The pixel units 22a/22b, the illumination units 13a/13b, the analog signal processing circuits 14B, the digital signal processing circuit 15B, the light adjustment computing unit 16B, the target value storage unit 17a/17b, and the OB value detector 18B are the same as the pixel unit 22, the illumination units 13, the analog signal processing circuits 14, the digital signal processing circuit 15, the light adjustment computing unit 16, the target value storage unit 17, and the OB value detector 18, respectively, according to the first embodiment.

The OB value storage units 18B-1/18B-2 are storage units for temporarily storing the OB values, which are acquired by the OB value detector 18B from the image signals generated by the pixel units 22a/22b and the measured light values acquired by the light adjustment computing unit 16B from the image signals. The OB value storage units 18B-1/18B-2 consist of, for example, a buffer memory.

The operations of the capsule medical apparatus 10B of Modification 1-2 will be described in detail below. One of the systems (hereinafter, referred to as a "first imaging system") is driven and thus the pixel unit 22a generates an image signal (hereinafter, a signal generated by the first imaging system is referred to as a "first image signal"). Once the first image signal is input to each of the OB value detector 18B and the light adjustment computing unit 16B via the analog signal processing circuit 14B and the digital signal processing circuit 15B, the OB value detector 18B acquires an OB value from the input first image signal (hereinafter, an OB value acquired from the first image signal is referred to as a "first OB value") and then inputs the first OB value to the light adjustment computing unit 16B. The light adjustment computing unit 16B acquires a measured light value by performing the light measurement process on the input first image signal (hereinafter, a measured light value acquired from a first image signal is referred to as a "first measure light value"). The light adjustment computing unit 16B temporarily stores the input first OB value and the acquired first measured light value in the OB value storage unit 18B-1.

Subsequently, the other imaging system (hereinafter, referred to as a "second imaging system") is driven and thus the pixel unit 22b generates an image signal (hereinafter, a signal generated by the second imaging system is referred to as a "second image signal"). Once the second image signal is input to each of the OB value detector 18B and the light adjustment computing unit 16B via the analog signal processing circuit 14B and the digital signal processing circuit 15B, the OB value detector 18B acquires an OB value from the input second image signal (hereinafter, an OB value acquired from the second image signal is referred to as a "second OB value") and then inputs the second OB value to the light adjustment computing unit 16B. The light adjustment computing unit 16B acquires a measured light value by performing the light measurement process on the input second image signal (hereinafter, a measured light value acquired from a second image signal is referred to as a "second measure light value"). The light adjustment computing unit 16B temporarily stores the input second OB value and the acquired second measured light value in the OB value storage unit 18B-2.

Next, the first imaging system is driven. The light adjustment computing unit 16B reads the first OB value and the first measured light value, which are previously stored, from the OB value storage unit 18B-1 and reads the target value from the target value storage unit 17a. According to these values, the light adjustment computing unit 16B drives the illumination unit 13a while performing light adjustment control on the illumination unit 13a. Simultaneously, the control circuit 11 generates the next first image signal by driving the pixel unit 22a. The thus generated first image signal is, as described above, input to the OB value detector 18B and the light adjustment computing unit 16B via the analog signal processing circuit 14B and the digital signal processing circuit 15B. The OB value detector 18B acquires, as described above, a first OB value from the input first image signal and then inputs the first image signal to the light adjustment computing unit 16B. The light adjustment computing unit 16B acquires, as described above, a first measured light value by performing the light measurement process on the input first image signal. The light adjustment computing unit 16B then updates the first OB value and the first measured light value in the OB value storage unit 18B-1 using the new first OB value and the first measured light value.

Subsequently, the second imaging system is driven. The light adjustment computing unit 16B reads the second OB value and the second measured light value, which are previously stored, from the OB value storage unit 18B-2 and reads the target value from the target value storage unit 17b. According to these values, the light adjustment computing unit 16B performs light adjustment control on the illumination unit 13b and drives the illumination unit 13b. Simultaneously, the control circuit 11 generates the next second image signal by driving the pixel unit 22b. The thus generated second image signal is, as described above, input to the OB value detector 18B and the light adjustment computing unit 16B via the analog signal processing circuit 14B and the digital signal processing circuit 15B. The OB value detector 18B acquires, as described above, a second OB value from the input second image signal and then inputs the second image signal to the light adjustment computing unit 16B. The light adjustment computing unit 16B acquires, as described above, a second measured light value by performing the light measurement process on the input second image signal. The light adjustment computing unit 16B then updates the second OB value and the second measured light value in the OB value storage unit 18B-2 using the new second OB value and the second measured light value.

Thereafter, by repeating the same operations, the imaging operation by the first imaging system and the imaging operation by the second imaging system are repeated alternately. The first/second image signals via the analog signal processing circuit 14B and the digital signal processing circuit 15B are input to the transmission circuit 19 and then are transmitted from the transmission circuit 19 by radio to the external receiving device 30.

As described above, in Modification 1-2, because the light adjustment mechanism is shared by multiple imaging systems, the internal configuration of the capsule medical apparatus 10B can be simplified. Other configurations, operations, and effects are the same as those of the above-described embodiment and Modification thereof and thus detailed descriptions thereof are omitted here.

Second Embodiment

A configuration and operations of an in-vivo information acquisition system according to a second embodiment of the present invention will be described in detail below using the drawings. Regarding configurations and operations in the following descriptions that are the same as those of the above-described embodiment and Modifications thereof, the above-described embodiment and Modifications thereof will be referred to and redundant descriptions will be omitted.

The in-vivo information acquisition system according to the second embodiment is the same as the in-vivo information acquisition system 1 according to the above-described first embodiment. In the second embodiment, however, a capsule medical apparatus 10C is used as a body-insertable apparatus.

Figure 9:
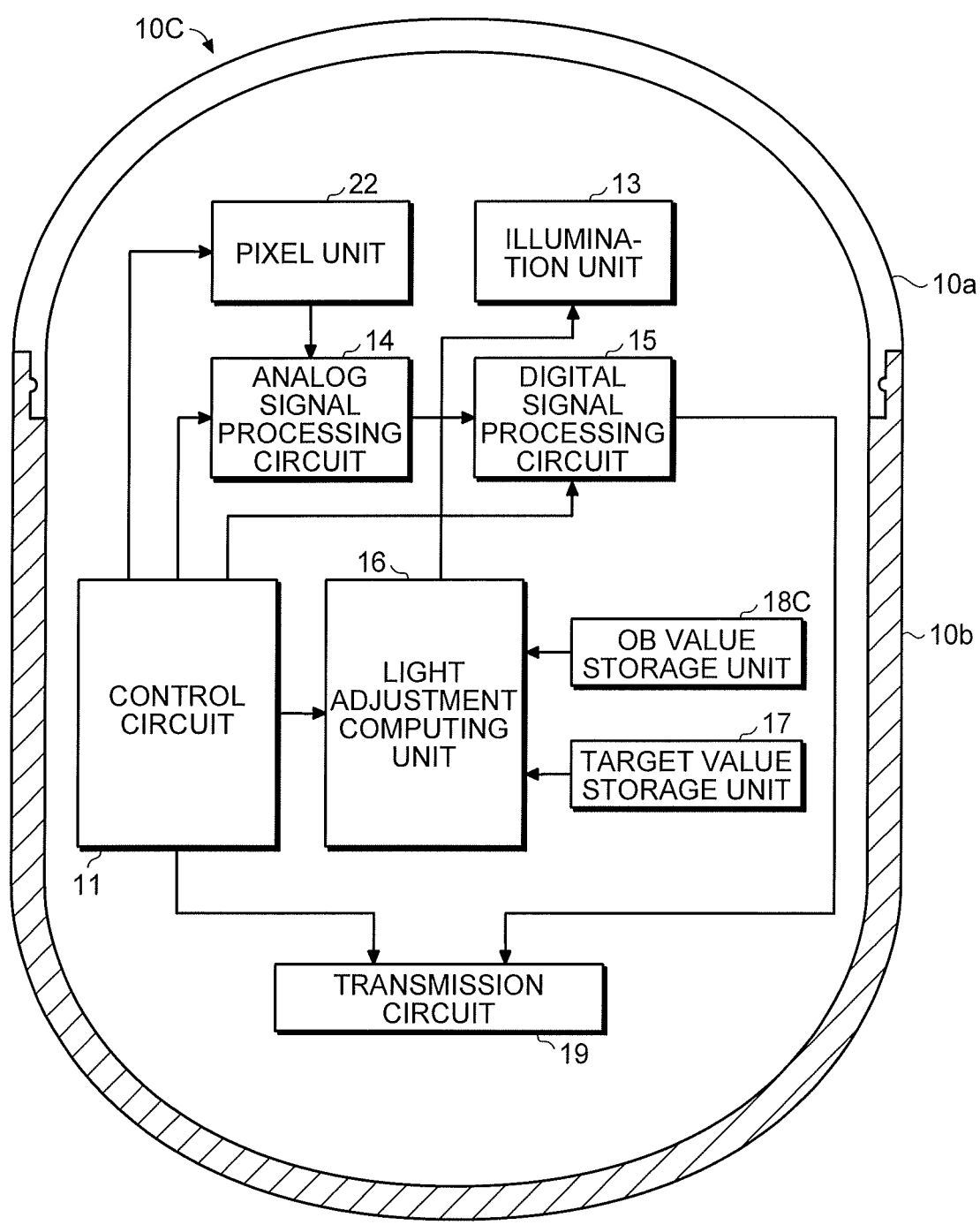
FIG. 9 is a block diagram of a general configuration of a capsule medical apparatus according to a second embodiment of the present invention.

FIG. 9 is a block diagram of a general configuration of the capsule medical apparatus 10C according to the second embodiment. As depicted in FIG. 9, in the capsule medical apparatus 10C, the OB value detector 18 of the capsule medical apparatus 10 according to the first embodiment is replaced by an OB value storage unit (a black level index storage unit) 18C.

The OB value storage unit 18C previously (for example, during production) stores an acquired OB value. The OB value can be acquired in the same manner as that of the first embodiment. Because, for example, as described above, the OB value is previously acquired during adjustment before shipment and the OB value is stored in the capsule medical apparatus 10C, it is not necessary to acquire an OB value each time an image is captured. Accordingly, the number of arithmetic operations in the capsule medical apparatus 10C can be reduced.

The operations of the capsule medical apparatus 10C according to the first embodiment can be achieved by replacing the OB value acquisition process at step S106 in the operations described using FIG. 6 in the first embodiment with reading of an OB value from the OB value storage unit 18C. Other configurations, operations, and effects are the same as those of the above-described embodiments and Modifications thereof; therefore, the detailed descriptions thereof are omitted here.

Modification 2-1

Figure 10:
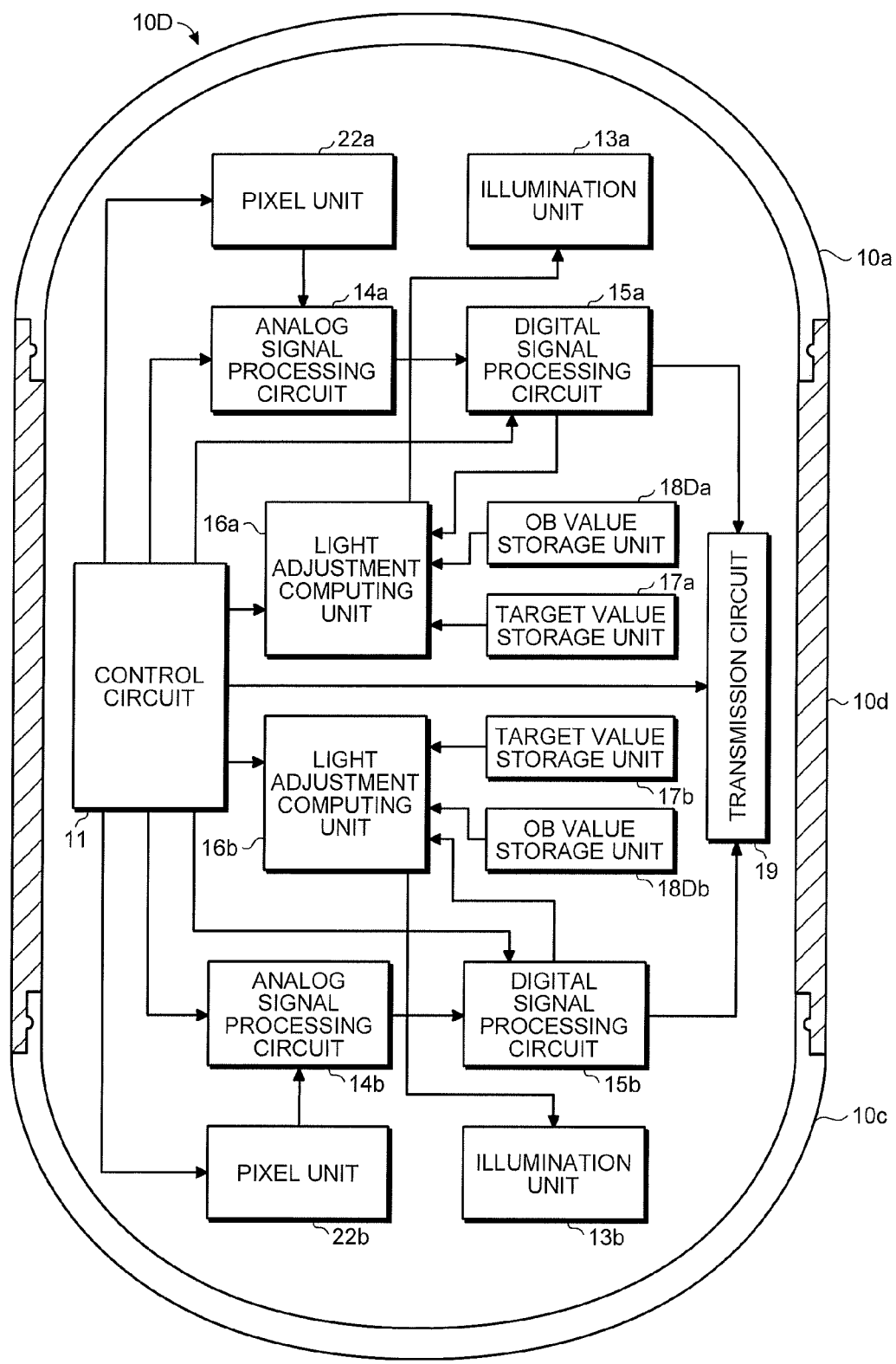
FIG. 10 is a block diagram of a general configuration of a capsule medical apparatus according to Modification 2-1 of the second embodiment of the present invention.

As depicted in FIG. 10 and as is in Modification 1-1 of the first embodiment, the capsule medical apparatus 10C according to the second embodiment can be applied to a capsule medical apparatus including multiple imaging systems each including an imaging device and an illumination unit, i.e., a pantoscopic capsule medical apparatus 10D. FIG. 10 is a block diagram of a general configuration of the capsule medical apparatus 10D of Modification 2-1 of the second embodiment.

OB value storage units 18Da/18Db in FIG. 10 are the same as the OB value storage unit 18C according to the second embodiment. The OB value storage unit 18Da stores a target value for performing light adjustment control on the illumination unit 13a and the OB value storage unit 18Db stores a target value for performing light adjustment control on the illumination unit 13b. Other configurations, operations, and effects are the same as those of the above-described embodiments and Modifications thereof; therefore, the detailed descriptions thereof are omitted here.

Modification 2-2

Figure 11:
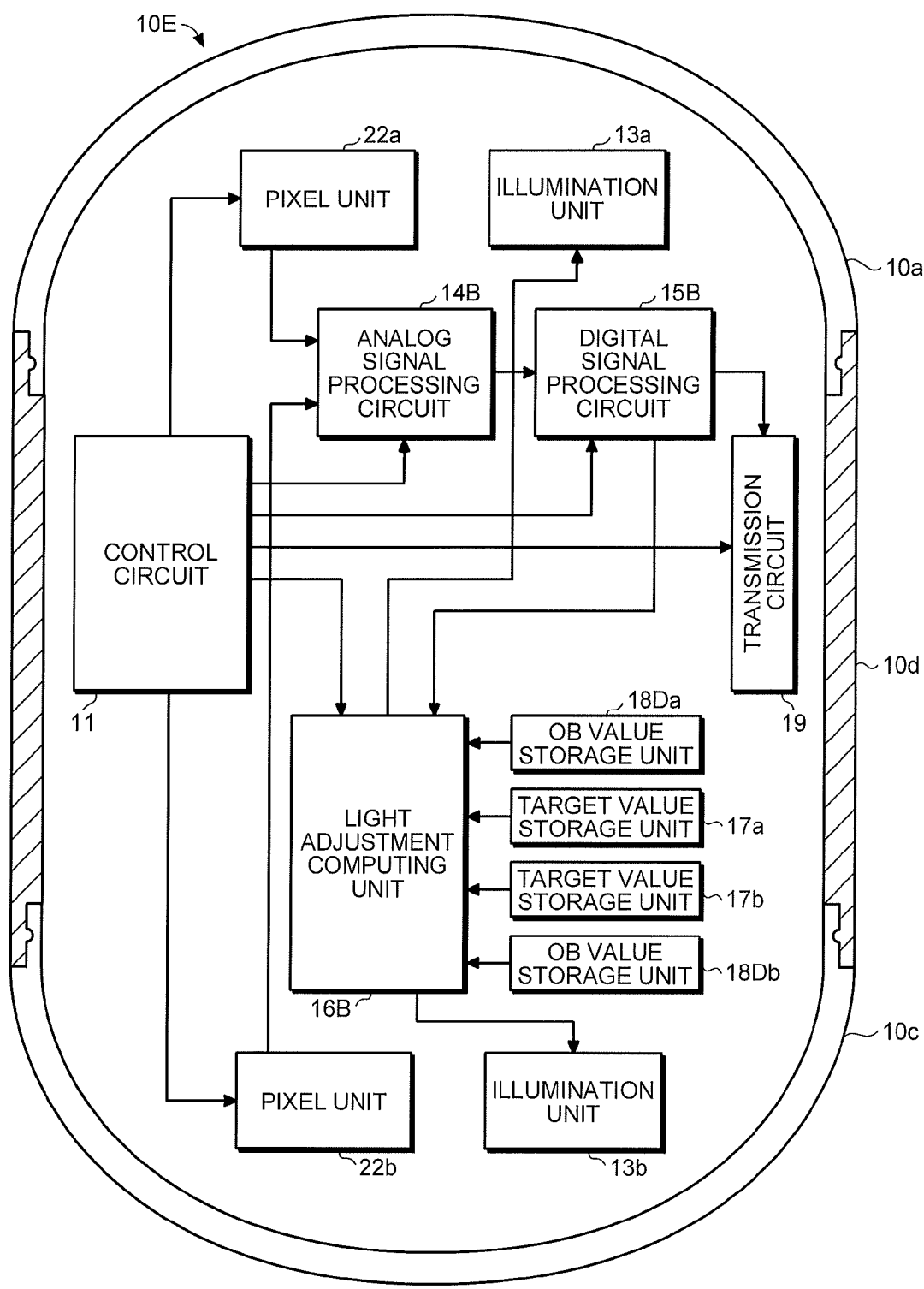
FIG. 11 is a block diagram of a general configuration of a capsule medical apparatus according to Modification 2-2 of the second embodiment of the present invention.

As depicted in FIG. 11 and as is in the second embodiment, the capsule medical apparatus 10C according to the second embodiment may be configured such that a light adjustment mechanism (a processing system may be included) is shared by multiple imaging systems. FIG. 11 is a block diagram of a general configuration of a capsule medical apparatus 10E according to Modification 2-2 of the second embodiment. Other configurations, operations, and effects are the same as those of the above-described embodiments and Modifications thereof, therefore, detailed descriptions thereof are omitted here.

Third Embodiment

A configuration and operations of an in-vivo information acquisition system according to a third embodiment of the present invention will be described in detail below using the drawings. Regarding configurations and operations in the following descriptions that are the same as those of the above-described embodiments and Modifications thereof, the above-described embodiments and Modifications thereof will be referred to and redundant descriptions will be omitted.

The in-vivo information acquisition system according to the third embodiment is the same as the in-vivo information acquisition system 1 according to the above-described first embodiment. In the third embodiment, however, the receiving device 30 or the OB correction process of the information processing apparatus 50 are as described below.

Figure 12:
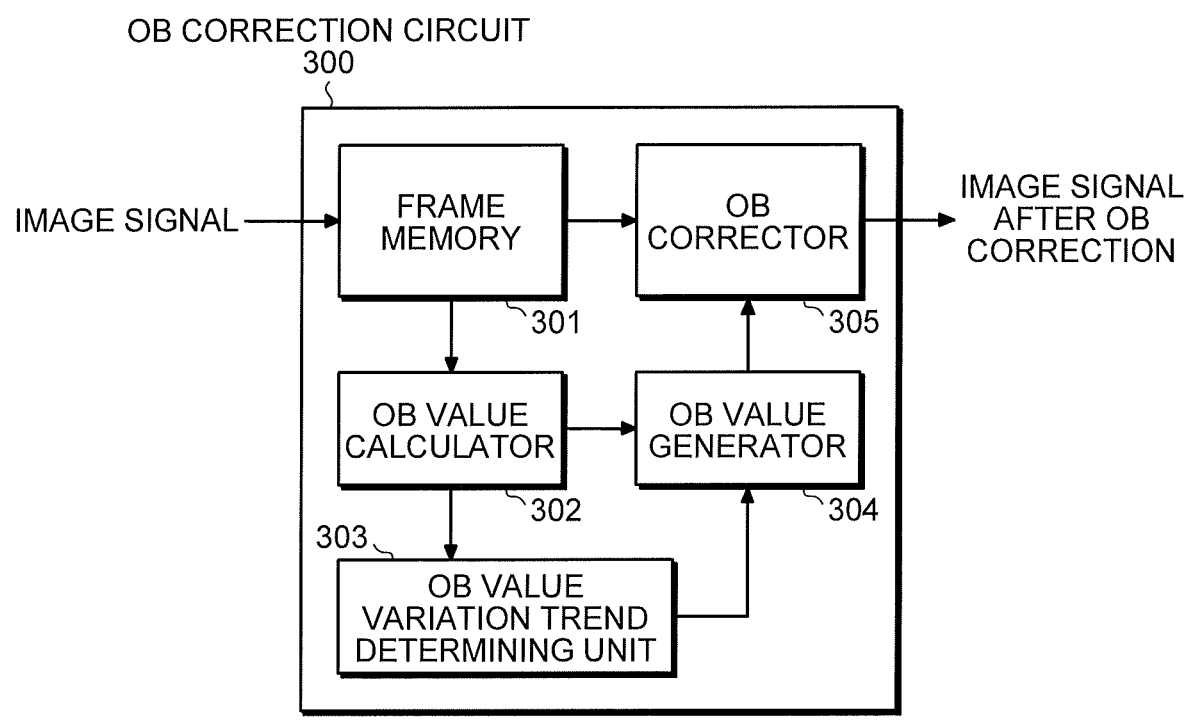
FIG. 12 is a schematic block diagram of a configuration of an OB correction circuit that performs an OB correction process according to a third embodiment of the present invention.

FIG. 12 is a schematic block diagram of a configuration of an OB correction circuit 300 that performs an OB correction process according to the third embodiment. The OB correction circuit 300 is installed in a signal processing circuit (not shown) of the receiving device 30 or in a CPU (not shown) of the information processing apparatus 50.

As depicted in FIG. 12, the OB correction circuit 300 includes a frame memory 301 that temporarily stores an input image signal; an OB value calculator 302 that calculates an OB value of each line from at least a part of an OB region R3 of the image signal stored in the frame memory 301; an OB-value variation trend determining unit 303 that determines OB-value variation trend in one frame from OB values of respective lines calculated by the OB value calculator 302; an OB value generator 304 that generates an OB value used for OB correction depending on the OB-value variation trend in one frame determined by the OB-value variation trend determining unit 303; and an OB corrector 305 that performs OB correction on the image signal, which is stored in the frame memory 301, according to the OB value generated by the OB value generator 304.

Figure 13:
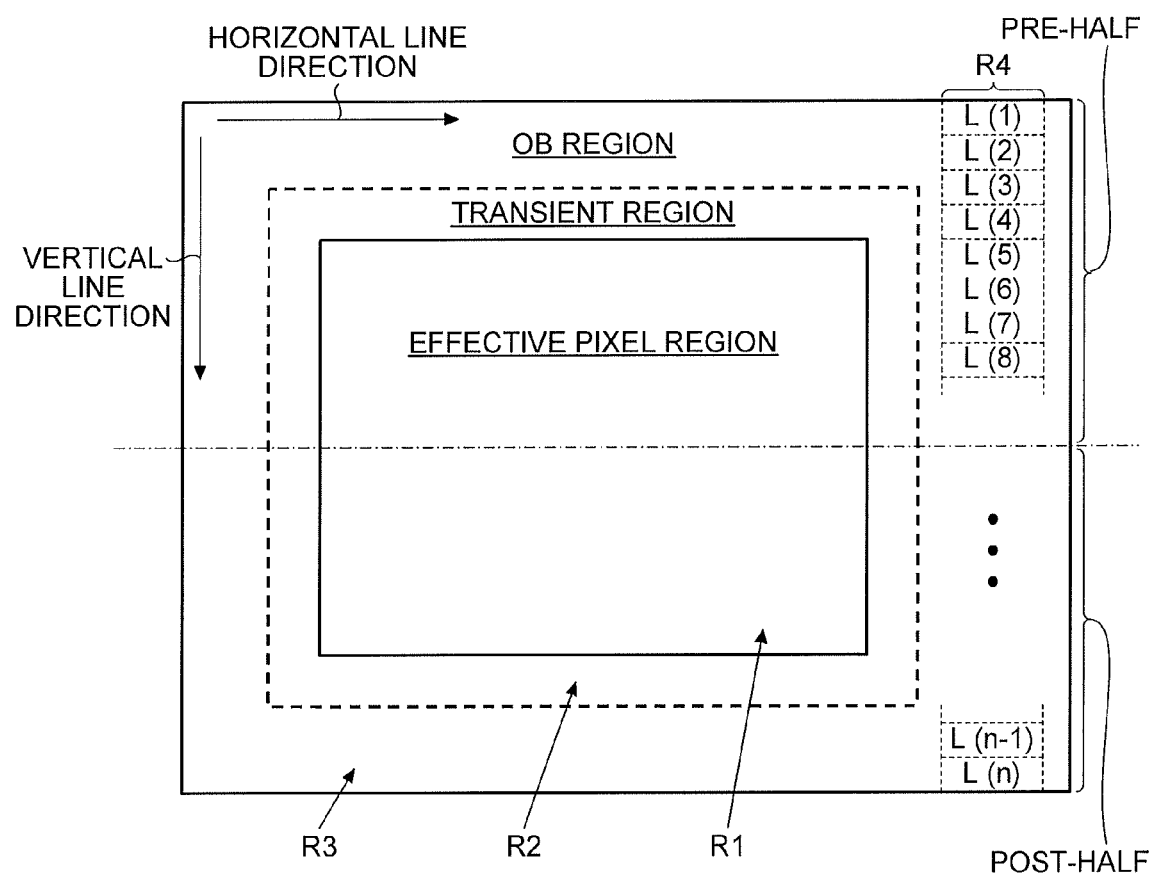
FIG. 13 is a diagram of an example of a configuration of an imaging device in the third embodiment of the present invention.

A process of calculating an OB value of each line, which is performed by the OB value calculator 302, and a process of determining OB-value variation trend in one frame, which is performed by the OB-value variation trend determining unit 303, will be described using FIG. 13. FIG. 13 is a diagram of an example of an image signal in the third embodiment. In FIG. 13, an image signal consists of n lines L(1) to L(n) in total.

As depicted in FIG. 13, the image signal includes an effective pixel region R1 that is effective as a subject in-vivo image, a transient region R2 around the effective pixel region R1, and an OB region R3. The OB value calculator 302 calculates an OB value of each line of the OB region R3 of the image signal, using pixel values of pixels arrayed in the vertical line direction and contained in a region R4.

The OB-value variation trend determining unit 303 calculates, regarding OB values calculated by the OB value calculator 302, an average value $A_{pre}$ of one or more lines in the pre-half of the image signal and an average value $A_{pos}$ of one or more lines in the post-half of the image signal and determined fluctuation of the black level in one frame from the absolute value ($|A_{pre}-A_{pos}|$) of the difference between these two average values $A_{pre}$ and $A_{pos}$. In other words, when the absolute value ($|A_{pre}-A_{pos}|$) of the two average values $A_{pre}$ and $A_{pos}$ is larger than a pre-set threshold Vth, the OB-value variation trend determining unit 303 determines that the black-level fluctuation in one frame is large. When the absolute value ($|A_{pre}-A_{pos}|$) is equal to or smaller than the threshold Vth, the OB-value variation trend determining unit 303 determines that the black-level fluctuation in one frame is small.

The OB value generator 304 generates an OB value used for OB correction according to the result of the determination by the OB-value variation trend determining unit 303 and inputs the OB value to the OB corrector 305. For example, when the OB-value variation trend determining unit 303 determines that the black-level fluctuation in one frame is large, the OB value generator 304 generates, as an OB value used for OB correction on each line, the OB value of each line that is calculated by the OB value calculator 302. In contrast, when the OB-value variation trend determining unit 303 determines that the black-level fluctuation in one frame is small, the OB value generator 304 generates, as an OB value for one frame, the average value of the OB values of all the lines calculated by the OB value calculator 302.

The OB corrector 305 reads an image signal line by line from the frame memory 301 and performs OB correction on the image signal using the OB value input from the OB value generator 304. Thereafter, the OB corrector 305 sends the image signal after the OB correction to the subsequent processing unit (not shown).

With the above-described configuration and the operations, in the third embodiment, even if only OB-value variations between continuous lines can be determined, the image after the OB correction is not significantly influenced by the OB-value variations and thus it can be a smooth image.

In the third embodiment, a case is taken as an example in which, when the OB-value variation trend determining unit 303 determines that the black-level fluctuation in one frame is large, OB correction is performed on each line using the OB value of each line. However, the present invention is not limited to this. For example, the OB value generator 304 may generate, as an OB value, an average value of OB values of multiple lines.

In addition, in the above description, an example is taken as an example, in which the third embodiment is applied to the first embodiment of the present invention. However, the present invention is not limited to this. The third embodiment can be applied to any of the above-described embodiments and Modifications thereof.

Fourth Embodiment

A configuration and operations of an in-vivo information acquisition system according to a fourth embodiment of the present invention will be described in detail below using the drawings. Regarding configurations and operations in the following descriptions that are the same as those of the above-described embodiments and Modifications thereof, the above-described embodiments and Modifications will be referred to and redundant descriptions will be omitted.

The in-vivo information acquisition system according to the fourth embodiment is the same as the in-vivo information acquisition system 1 according to the above-described first embodiment. In the fourth embodiment, however, an image signal transmitted by the capsule medical apparatus 10 from the transmission circuit 19 is as depicted in FIG. 14. FIG. 14 is a diagram illustrating a conception of an image signal of one frame transmitted by the capsule medical apparatus 10 in the fourth embodiment.

When OB correction is performed in a configuration (for example, the receiving device 30 or the information processing apparatus 50: hereinafter, the receiving device 30) other than the capsule medical apparatus 10, it is necessary to transmit information for calculating an OB value to the receiving device 30. Regarding transmission of an image signal, a vertical synchronization signal and a horizontal synchronization signal for synchronization between the transmission side and the receiving side for data exchange are embedded in a portion of the image signal corresponding to the OB region R13. However, when a vertical synchronization signal and a horizontal synchronization signal are embedded in the OB region R13, the pixel values of the OB region R13 may not be transmitted to the receiving device 30 and thus the receiving device 30 may not calculate an OB value.

For this reason, in the fourth embodiment, a configuration is employed in which, an image signal is transmitted that contains a vertical synchronization signal and a horizontal synchronization signal in, instead of the OB region R13, a transient region R12 around an effective pixel region R11. Accordingly, the vertical synchronization signal and the horizontal synchronization signal can be transmitted with the image signal without missing the pixel values of the OB region R13.

However, the present invention is not limited to this. For example, an OB value acquired by the capsule medical apparatus 10 may be contained in an OB region R13 or a transient region R12 of an image signal and a vertical synchronization signal and a horizontal synchronization signal may be contained in the remaining region of the OB region R13 and/or the transient region R12. Accordingly, even if the pixel values of the OB region R13 are not transmitted, OB correction can be performed using the OB value received in the receiving device 30.

In the above descriptions, a case in which the fourth embodiment is applied to the first embedment of the present invention is taken as an example. However, the present invention is not limited to this. The fourth embodiment can be applied to the any of the above-described embodiments and Modifications thereof.

In the embodiments described above, the amount of light from the illumination unit can be adjusted based on the pixel values of an image signal of an effective pixel region and pixel values of the image signal of an optical black region. Thus, a body-insertable apparatus and an in-vivo information acquisition system can be realized that can perform a stable light adjustment process using a small number of arithmetic operations.

The embodiments as described above are just examples of the present invention and thus do not limit the invention. It should be obvious that the above description could make the various changes according to specifications and the like within the scope of the invention and other various embodiments within the scope of the invention.

What is claimed is:

1. A body-insertable apparatus to be inserted into a subject, the body-insertable apparatus comprising:
    an illumination unit that illuminates an inside of the subject;
    an imaging device comprising:
        an effective pixel region on which an optical image of the inside of the subject illuminated by the illumination unit is formed; and
        an optical black region at which the optical image is shielded,
        wherein the effective pixel region has a predetermined size; and
    a light adjustment control unit that adjusts an amount of light from the illumination unit to the effective pixel region based on pixel values of the effective pixel region of an image signal and pixel values of the optical black region of the image signal, wherein the light adjustment control unit comprises:
        a measured light value calculating unit that calculates a measured light value from the effective pixel region of the image signal;
        a target value storage unit that stores a target value for adjusting the amount of light emitted by the illumination unit;
        a black level detecting unit that acquires a black level index of a black level of the image signal based on one or more pixel values contained in the optical black region; and
        a light adjustment computing unit that adjusts the amount of light from the illumination unit based on the measured light value calculated by the measured light value calculating unit, the target value stored in the target value storage unit, and the black level index acquired by the black level detecting unit.

2. The body-insertable apparatus according to claim 1, wherein the light adjustment control unit corrects the measured light value or the target value based on the black level index.

3. The body-insertable apparatus according to claim 1, wherein the light adjustment control unit corrects the target value based on the black level index, compares the target value that has been corrected with the measured light value, and adjusts the amount of light from the illumination unit based on a result of the comparison.

4. The body-insertable apparatus according to claim 1, wherein the light adjustment control unit corrects the measured light value based on the black level index, compares the measured light value that has been corrected with the target value, and adjusts the amount of light from the illumination unit based on the comparison.

5. A body-insertable apparatus to be inserted into a subject, the body-insertable apparatus comprising:
    an illumination unit that illuminates an inside of the subject;
    an imaging device comprising:
        an effective pixel region on which an optical image of the inside of the subject illuminated by the illumination unit is formed; and
        an optical black region at which the optical image is shielded,
        wherein the effective pixel region has a predetermined size; and
    a light adjustment control unit that adjusts an amount of light from the illumination unit to the effective pixel region based on pixel values of the effective pixel region of an image signal and pixel values of the optical black region of the image signal, wherein the light adjustment control unit comprises:
        a measured light value calculating unit that calculates a measured light value from the effective pixel region of the image signal;
        a target value storage unit that stores a target value for adjusting the amount of light emitted by the illumination unit;
        a black level index storage unit that stores a black level index of a black level of the optical black region of the image signal; and
        a light adjustment computing unit that adjusts the amount of light from the illumination unit based on the measured light value calculated by the measured light value calculating unit, the target value stored in the target value storage unit, and the black level index stored in the black level index storage unit.

6. An in-vivo information acquisition system comprising:
    a body-insertable apparatus comprising:
        an illumination unit that illuminates an inside of a subject;
        an imaging device comprising:
            an effective pixel region on which an optical image of the inside of the subject illuminated by the illumination unit; and
            an optical black region at which the optical image is shielded,
            wherein the effective pixel region has a predetermined size; and
        a light adjustment control unit that adjusts an amount of light from the illumination unit to the effective pixel region based on pixel values of the effective pixel region of an image signal and pixel values of the optical black region of the image signal; and
    an external device that receives the image signal transmitted from the body insertable apparatus and displays the image signal, wherein the external device comprises a correcting unit that corrects a black level of the image signal, wherein the correcting unit comprises:
        a frame memory that stores the image signal of one frame;
        a black level correcting unit that corrects the black level of the image signal stored in the frame memory;
        a black level index calculating unit that calculates a black level index of each line of the image signal stored in the frame memory;
        a variation trend determination unit that determines trends in variations of the black level index of the image signal of one frame; and
        a black level index generating unit that generates a black level index, which is used by the black level correcting unit to correct the black level of the image signal, based on a result of the determination by the variation trend determination unit.

* * * * *